United States Patent [19]

Tarte

[11] Patent Number: 5,786,527
[45] Date of Patent: Jul. 28, 1998

[54] METHOD AND APPARATUS FOR TESTING SOIL CONTAMINATION

[76] Inventor: André Tarte, 540 Morin, Longueuil (Québec), Canada, J4L 3Z7

[21] Appl. No.: 718,505

[22] PCT Filed: Apr. 12, 1995

[86] PCT No.: PCT/CA95/00198
 § 371 Date: Oct. 4, 1996
 § 102(e) Date: Oct. 4, 1996

[87] PCT Pub. No.: WO95/27911
 PCT Pub. Date: Oct. 19, 1995

[30] Foreign Application Priority Data

Apr. 12, 1994 [GB] United Kingdom ............... 9407200

[51] Int. Cl.$^6$ ............................ G01N 1/24; G01N 33/24
[52] U.S. Cl. ................... 73/19.01; 73/864.74; 73/864.43
[58] Field of Search ............... 73/19.01, 19.12, 73/31.07, 864.41, 864.43, 864.81, 864.74, 864.33; 195/21, 59

[56] References Cited

U.S. PATENT DOCUMENTS

| | | | |
|---|---|---|---|
| 3,685,345 | 8/1972 | Wise | 73/19.1 |
| 4,335,622 | 6/1982 | Bartz | 73/864.74 |
| 4,452,091 | 6/1984 | Richers | 73/864.74 |
| 4,804,050 | 2/1989 | Kerfoot | 73/864.74 |

Primary Examiner—Michael Brock
Attorney, Agent, or Firm—François Martineau

[57] ABSTRACT

The invention relates to a method of measuring the degree of contamination of a soil volume by a contaminant which has a volatile constituent. The steps of the method include the injection of a non-contaminated gas into this soil volume for a period of time sufficient for a measurement of the volatile constituent to be reduced, and the subsequent measuring of the rate of increase of the concentration of the volatile constituent in this soil volume.

7 Claims, 6 Drawing Sheets

_Fig. 6C_

_Fig. 7A_

METHOD AND APPARATUS FOR TESTING SOIL CONTAMINATION

The present invention relates to a method and apparatus, and more particularly, relates to a method and apparatus for the testing of soil contamination.

The testing of soil for many reasons is well known in the art. One reason for such testing of the soil is to determine the presence of contaminants which may be the subject of environmental concern. For example, it is well known that a substantial amount of pollution has been caused by the leakage of tanks storing various liquids. One particular problem is the wide spread use of underground storage tanks for various petroleum products with it being known that many of these tanks leak due to corrosion and/or other reasons.

Many different types of proposals have been advanced in the art regarding the testing of the soil for contamination. One common type of testing involves the physical removal of a soil sample and forwarding of the same to a suitable laboratory for analysis. Disadvantages encountered with this method include the delays which are involved for the analysis of the samples and furthermore, the procedure normally involves a fairly substantial expense. Other known methods and apparati for the testing of soil are shown, for example, in U.S. Pat. No. 5,050,425 which shows an apparatus and method for measuring the presence of a volatile constituent of a sample of ground water or soil mixed with water. A different type of in-situ testing for contaminants is shown in U.S. Pat. No. 5,246,862 wherein a penetrometer is used to determine chemical contaminants in soil using calorimetric techniques.

A common problem associated with the known methods is the difficulty to determine the spreading or extension of the contamination efficiently and rapidly. Thus, while an absolute test may provide a certain reading, the reading is not necessarily indicative of the pollution extension insofar as its proximity to the actual source of pollution. Thus, assuming the example of an hydrocarbon leakage, the relative presence in a sample of the hydrocarbon does not necessarily indicate its proximity to the original source of pollution since migration of the hydrocarbon can and does occur.

A further problem which arises is that, even after the offending source of contamination has been identified, often a large amount of soil is removed to clean up the pollution. Again, when information is not known as to the degree of pollution, frequently more soil is removed than required resulting in substantially higher costs.

A further problem, particularly when evaluating the vapor or gaseous phase of a contaminant such as gasoline, is the inconsistency of results obtained. A concentration of organic vapors in a soil does not necessarily correlate effectively to the hydrocarbon contamination. The vapors can travel in the soil from the site of original contamination and can lead to false positive testing. Also, this testing does not necessarily give a direct relationship between the concentration of the organic vapor in the soil and the concentration of the hydrocarbon in the area.

U.S. Pat. No. 5,010,776 also discloses a method and system for detecting a contaminant wherein a probe collects a fluids sample from the contaminated medium. In the method, a fluid sample is taken by a carrier gas for analysis of the contaminant. The reference evaluates the partial pressure of the contaminant with a semi permeable membrane.

It is also known from U.S. Pat. No. 3,685,534 to circulate a fluid into repetitive contacts with soil and then measure the concentration of the selected fluid in the circulating fluid after a substantial period of time. A tool for accomplishing this is shown in U.S. Pat. No. 3,857,289.

For these reasons, the evaluation of organic vapors in the soil has, to date, only been considered a preliminary evaluation tool.

The displacement of the gaseous phase or vapor in a soil contaminated with hydrocarbons is influenced by many parameters such as the nature of the soil (its porosity, organic content, moisture content, the nature of the contaminant, etc.) When a liquid hydrocarbon is introduced in a soil, the contamination will spread according to the nature of the geological formation. Generally, the liquid portion of the hydrocarbon contaminant dispersion can occur under the influence of gravitational forces and also by capillary action.

It is an object of the present invention to provide a method for determining the relative presence of a fluid contaminant in a soil.

It is a further object of the present invention to provide a method, using the presence of a vapor constituent, to evaluate the degree of hydrocarbon contamination in a soil.

It is a further object of the present invention to provide a device suitable for the testing of soil for the presence of a contaminant.

It is a further object of the present invention to provide a method for the testing of soil samples in order to determine the degree of contamination of the soil.

According to one aspect of the present invention, there is provided a method for determining the relative presence of a first fluid in a soil volume, the method including the step of treating soil volume by injecting a second fluid into the soil volume for a period of time sufficient to reduce the presence of the first fluid, the method being characterized by the step of measuring the rate of increase of the concentration of the first fluid in the soil volume.

There is also provided a method of measuring the degree of contamination of a soil volume by a contaminant which has a volatile constituent, the method comprising the steps of injecting a gas into the soil volume for a period of time sufficient for a measurement of the concentration of the volatile constituent to be reduced, and subsequently measuring the rate of increase of the concentration of the volatile constituent in the soil volume.

In a still further aspect of the present invention, there is provided a method for determining the degree of contamination of soil volume by a hydrocarbon having a volatile constituent, a method comprising the steps of measuring the concentration of the volatile constituent in the soil volume, injecting a non-contaminated gas into the soil volume while continuing to measure the concentration of the volatile constituent until the concentration level of the volatile constituent remains relatively stable, reducing the rate of injection of the non-contaminated gas, and measuring the rate of increase of the concentration of the volatile constituent.

There is also provided a testing device which comprises a first conduit having a first fluid passageway therein and a fluid outlet which is in fluid communication with the first fluid passageway and which fluid outlet is located proximate one end of the conduit. A probe head is secured to the first conduit and it is at least partially retractable within the conduit. The probe head includes a fluid passageway in fluid communication with a fluid outlet. A second conduit having a second fluid passageway is mounted within the first conduit, the second fluid passageway being in fluid communication with the fluid passageway in the probe head.

In greater detail, in one specific aspect of the present invention, there is provided a novel method for the measurement of soil contamination by a contaminant which has a volatile constituent. Typically, such a contaminant might be a hydrocarbon with one of the common problems being that of petroleum contamination caused by leakage from underground storage tanks. To date, it has been impossible to determine a correlation between the concentration of volatile compounds in the soil and the degree of contamination. In one method of the instant invention, a soil testing device is used to provide means for injecting the area to be tested with a first gas which for purposes of convenience may be purified air.

The injection of the purified air can, in some instance, be considered to be a flushing or purging of the area. This step is carried out for a period of time sufficient to desirably achieve a relatively constant measurement of the contaminant vapor. This period of time will usually extend from between one to ten minutes although it will be understood that the time may vary depending upon the particular contaminant being tested and other parameters.

Once the reading of the contaminant concentration level is relatively stable, the injection of the purified air can either be continued, stopped or lowered. It is preferred that some flow be continued such that there will be sufficient pressure for the vapor to be carried to be tested. It is at this point that one can then determine the degree of contamination by measuring either the rate at which the concentration of the volatile constituent increases or the final level of the concentration of the volatile constituent.

With respect to the above, it will be understood that one can mathematically calculate the level of the concentration of the volatile constituent by also measuring the rate at which the concentration increases.

The method of the present invention can be utilized both for in situ testing and laboratory testing. Thus, for in situ testing one can utilize a suitable testing device which is inserted into the soil and which testing device would have means for injecting air into the soil volume to be tested and for withdrawing vapors. A preferred embodiment of such a device is described hereinbelow.

The invention can also be used for testing of soil samples which have been removed. Since the tests provide results within a matter of minutes, one could utilize the method of the present invention at a site where it is desired to test various samples. One such use could, for example, be at a site where contaminated soil is being removed and one wishes to test the soil to determine to what extent it needs to be removed.

The actual testing of the concentration of the vapors or gas can be carried out by many different types of commercially available testers. There are, for example, commercially available photoionization detectors and infrared spectra photometers.

The type of soil containing the contamination can be important in the sense that different readings will be obtained from different types of soils as will be shown hereinbelow. In certain instances, and due to the capability of some of the portable test equipment, rates of change of the concentration of the volatile constituent may be utilized without waiting for relative stabilization. Mathematically, one is able to correlate these rates of changes to the degree of contamination.

During the injection of the purified air or other gas, one preferably uses a relatively low pressure so as not to disturb the soil sample.

The invention, as previously discussed, is very suitable for measuring the presence of a contaminant such as gasoline having a volatile constituent. However, it will also be understood that the method could also be utilized using other fluids including liquids.

Having thus generally described the invention, reference will be made to the accompanying drawings illustrating embodiments thereof, in which.

Figures 1, 2, 3, 4, 5:
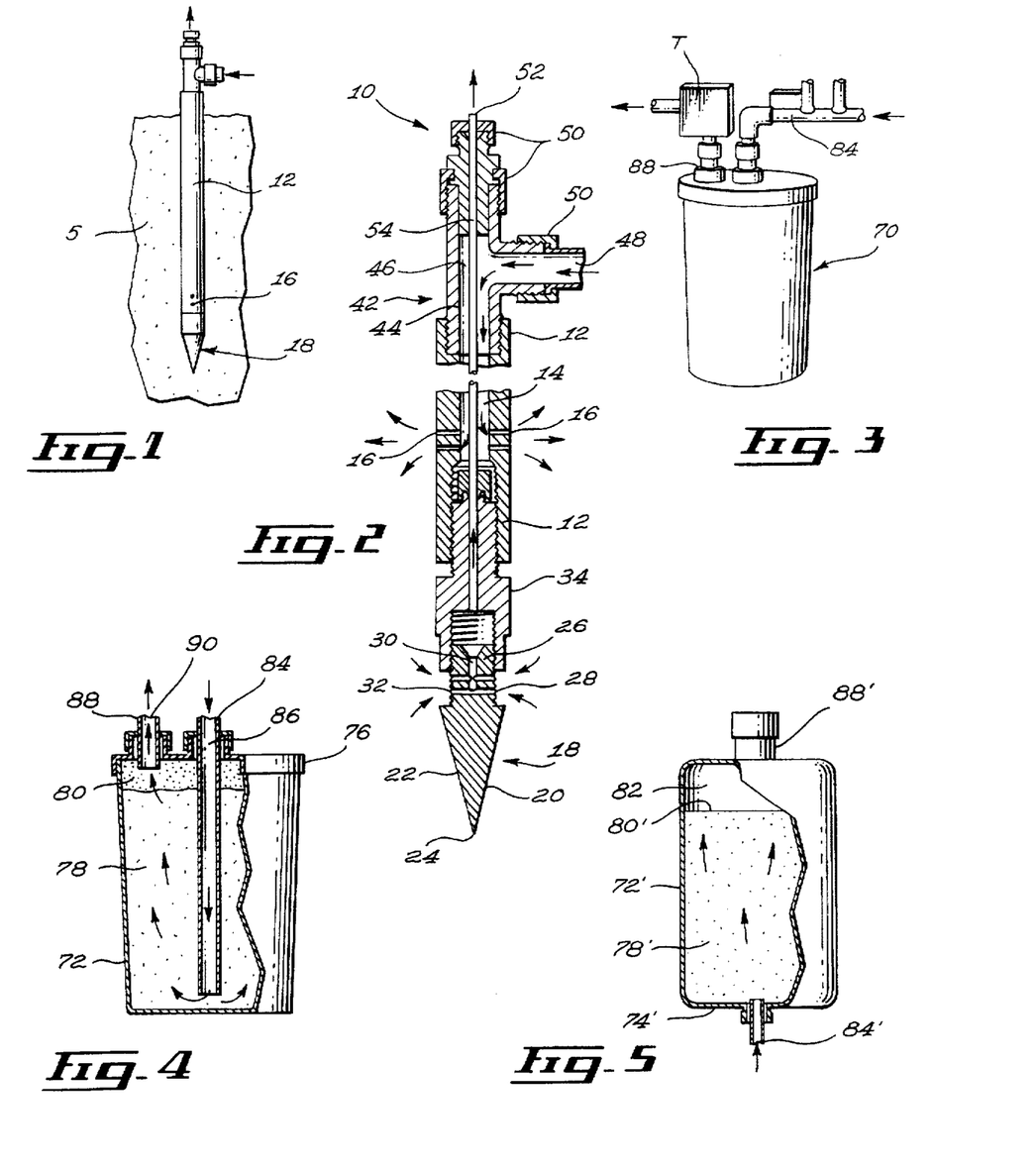
FIG. 1 is a side elevational view illustrating use of the device of the present invention.
FIG. 2 is a side sectional view of the device of the present invention.
FIG. 3 is a perspective view of one embodiment of a testing apparatus.
FIG. 4 is a side view, partially in section, of the testing apparatus of FIG. 3.
FIG. 5 is a sectional view of a further embodiment of a testing apparatus according to the present invention.

Referring to the drawings in greater detail and by reference characters thereto, there is illustrated a device generally designated by reference numeral 10. Device 10 includes an outer cylindrical conduit 12 having an interior axially extending passageway 14. Located near the lower portion of conduit 12 there are provided a plurality of radially extending passageways 16 which are in fluid communication with axial passageway 14.

Located at the lower extremity of conduit 12 is a probe tip assembly generally designated by reference numeral 18. Probe tip assembly 18 includes a lower portion having tapered side walls 20 and 22 to form a point 24 for soil penetration.

Probe tip 18 also includes an upper cylindrical portion 26 which has exterior screw threads 28 thereon. Cylindrical portion also includes an interior axial passageway 30 and a plurality of radially extending passageways 32 which are in fluid communication with axial passageway 30.

Cylindrical portion 26 is screw threadedly engaged with an adaptor 34 which in turn is screw threadedly engaged with the lower end of conduit 12. In this respect, adaptor 34 is screw threadedly engaged in a conventional manner with conduit 12 while probe tip 18 is reverse screw threadedly engaged with adaptor 34.

At the upper end of conduit 12, there is provided a T adaptor generally designated by reference numeral 42. T adaptor 42 includes an outer housing 44 and has an axially extending passageway 46 extending therethrough with a transverse passageway 48 being in fluid communication therewith. T adaptor 42 is screw threadedly engaged with conduit 12 and there are provided conventional connecting fittings which are designated by reference numeral 50. Extending through axial passageway 46 of T adaptor 42 and through axial passageway 14 of conduit 12 is an interior conduit 52 which has an interior passageway 54 therein. Interior conduit 52 is connected to probe tip 18 such that continuous fluid communication is provided between passageway 30 of cylindrical portion 26 and passageway 54 of inner conduit 52.

In operation, device 10 is inserted in a soil 5 which is to be tested. During insertion, probe tip 18 is fully screw threadedly engaged with adaptor 34—i.e. all of cylindrical portion 26 is within adaptor 34 and thus, radially passageways 32 are also covered by adaptor 34.

When inserted to the desired depth, rotation of conduit 12 will cause probe tip 18 to assume its extended position as shown in FIG. 2—probe tip 18, being in the soil 5, will tend not to rotate. Subsequently, a first fluid such as air is introduced through passageways 48 and 46 to radial passageways 16.

Monitoring of the gaseous contaminant is achieved by intake of gas through radially passageways 32 wherein the gas will flow through passageway 30 and passageway 54 of conduit 52 to a suitable testing apparatus (not shown).

The pumping of pure air is continued for a period of time sufficient that the measurement of the contaminant vapor from soil 5 is at a relatively stable or constant level. Subsequently, the rate of injection of air is reduced while the measurement of the contaminant is continued and the rate of increase of the contaminant level as measured in the area of the probe is a function of the degree of contamination in the soil.

Turning to FIGS. 3 and 4, there is illustrated a test apparatus for the testing of contaminated soil. The apparatus includes a container 70 having a cylindrical side wall 72 extending upwardly from a base 74. A cover member 76 is also provided.

A contaminated soil volume 78 is placed within container 70 and a filter medium 80 such as sand is then placed on top of the contaminated soil 78.

Extending through cover 76 is an inlet conduit 84 connected to a source (not shown) of a first fluid such as air. The air will enter through passageway 86 of inlet conduit 84. An outlet conduit 88 having interior passageway 90 is also provided.

In operation, in a manner similar to the previously described embodiment, filtered air is introduced through inlet conduit 84 and outlet conduit 88 is connected to a suitable contaminant measuring or testing device T. Filtered air is continually pumped through conduit 84 until a relatively consistent reading of the level of concentration of the contaminant in the soil is obtained. Subsequently, the pumping of air is reduced and the rate of increase of the presence of the contaminant is measured by testing device T. This provides an indication of degree of contamination of the soil 78.

In FIG. 5, a embodiment similar to that of FIGS. 3 and 4 is illustrated wherein a container 74' having contaminated soil 78' therein for testing. Air inlet 84' is provided at the bottom of the container while a filter is placed on top of contaminated soil 78'. An air space 82 is provided as well as a passageway 90' for exit to the testing device.

Figure 6A:
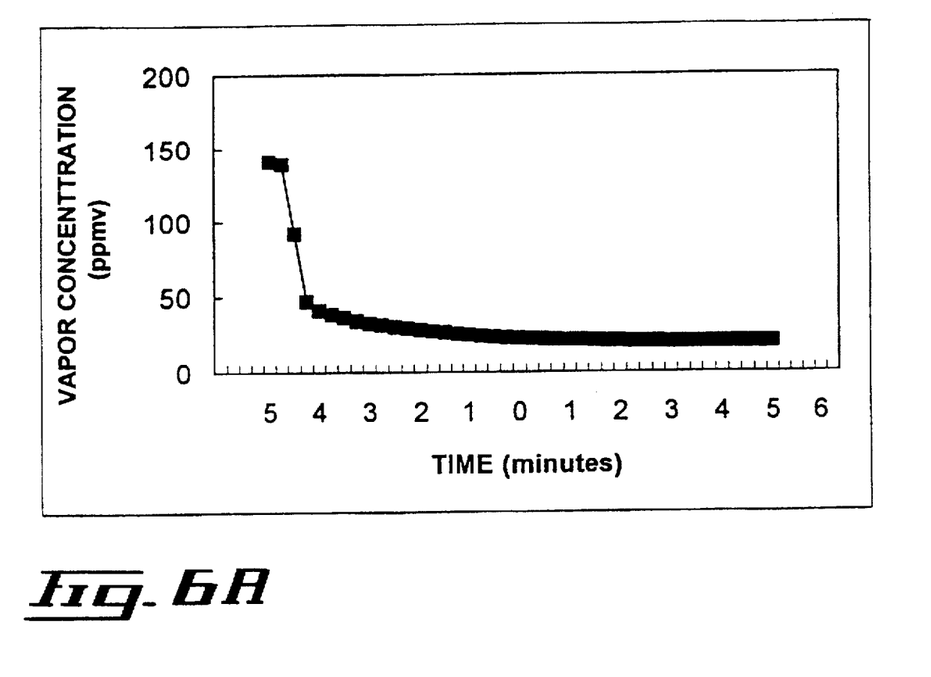
FIGS. 6A, 6B and 6C are graphs of in situ readings of soil taken at depths of 0.6; 1.2 and 1.8M respectively.
Figure 6B:
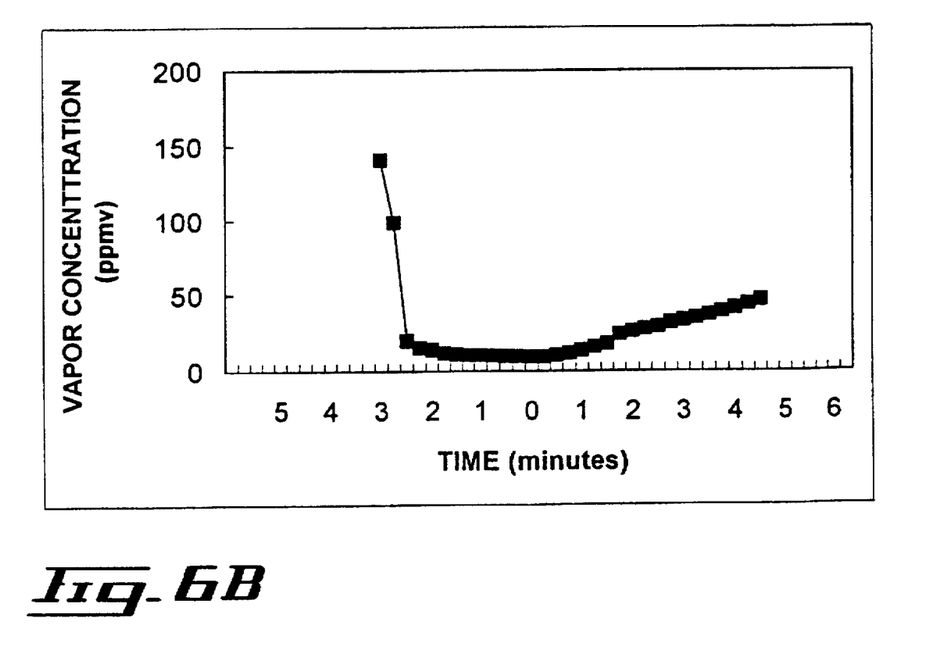
Figure 6C:
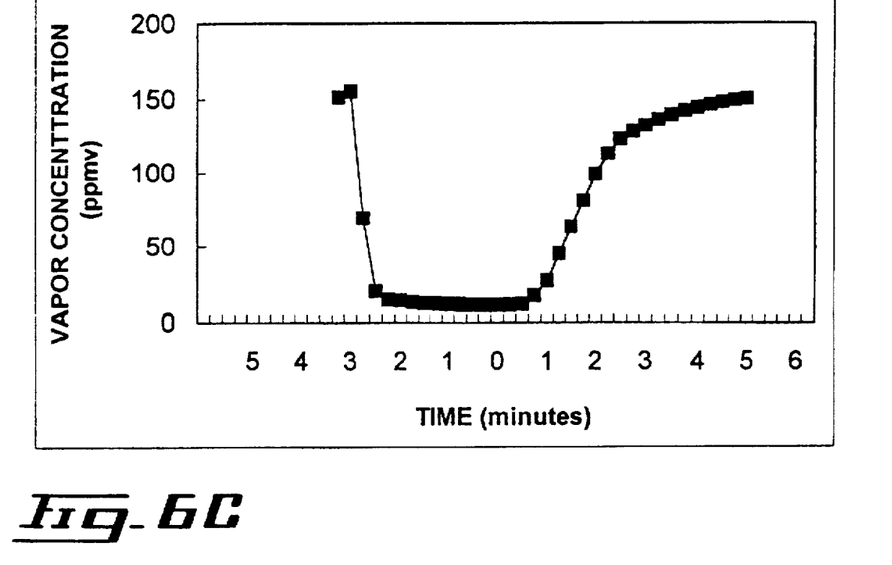

FIGS. 6A, 6B and 6C are graphs of readings taken near a first underground storage tank for gasoline. FIG. 6A was taken at a depth of 0.6 meters; FIG. 6B at a depth of 1.2 meters; and FIG. 6C at a depth of 1.8 meters.

As will be seen in FIG. 6A, the initial concentration reading was approximately 150 ppm which, following injection of purified air for 5 minutes lowered to a relatively stable level in the region of 20 ppm. The flow rate of air during this period was 2 li/min. Subsequently, at time 0, the flow rate was reduced to 0.5 li/min while the concentration continued to be monitored. As will be noted, there was little if any increase in concentration of the vapor indicating minor, if any, contamination.

FIG. 6B, taken at a depth of 1.2M, also gave an initial reading of approximately 150 ppm of contaminant. As will be noted, within 3 minutes of injecting air at the rate of 2 li/min the concentration level was stable and the injection rate of air was lowered to 0.5 li/min. It will be noted, that the concentration level increased at a moderate rate.

Turning to FIG. 6C, taken at a depth of 1.8M, again an initial reading in the area of 150 ppm of a vapor phase contaminant was measured. Air was injected at the rate of 2 li/min. and the concentration level stabilized rapidly. The rate of injection there was then lowered to 0.5 li/min; as will be seen, the concentration rate increased dramatically back up to the area of 150 ppm indicating a high degree of contamination at this level.

Figure 7A:
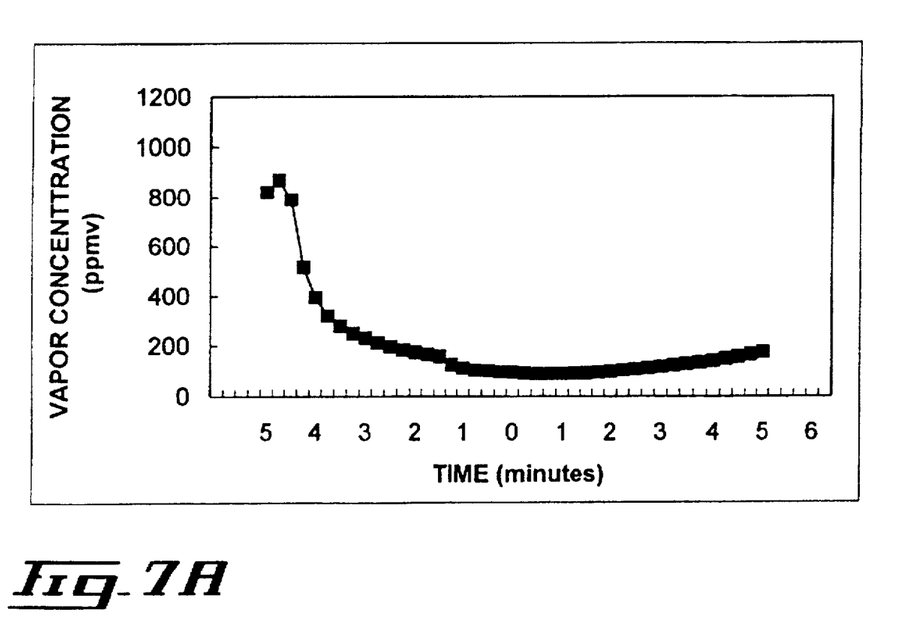
FIGS. 7A, 7B and 7C are graphs of readings taken at a second site at depths of 0.6; 1.2 and 1.8M respectively.
Figure 7B:
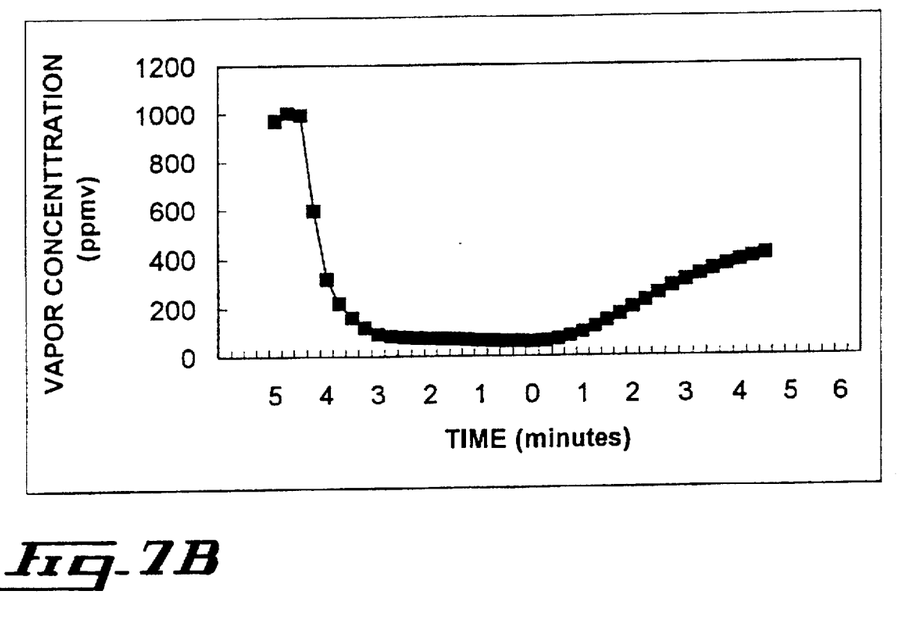
Figure 7C:
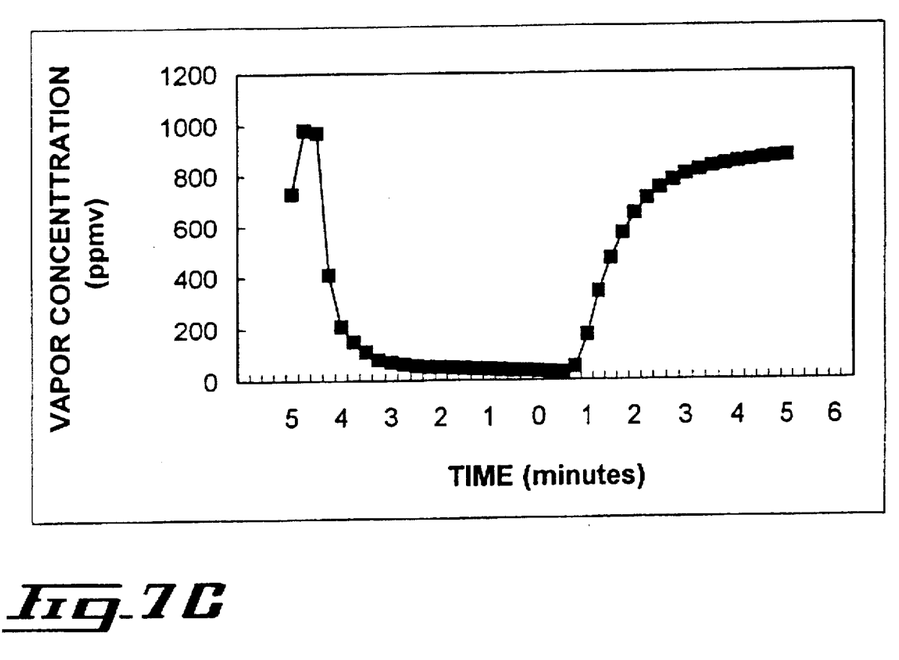

FIGS. 7A, 7B and 7C are readings taken at a second point at the same site near an underground gasoline storage tank. Again, the readings were taken at 0.6; 1.2 and 1.8M. As will be seen, despite initial readings which are close to each other, the testing indicates that the highest degree of contamination is at a level of 1.8M.

Figure 8A:
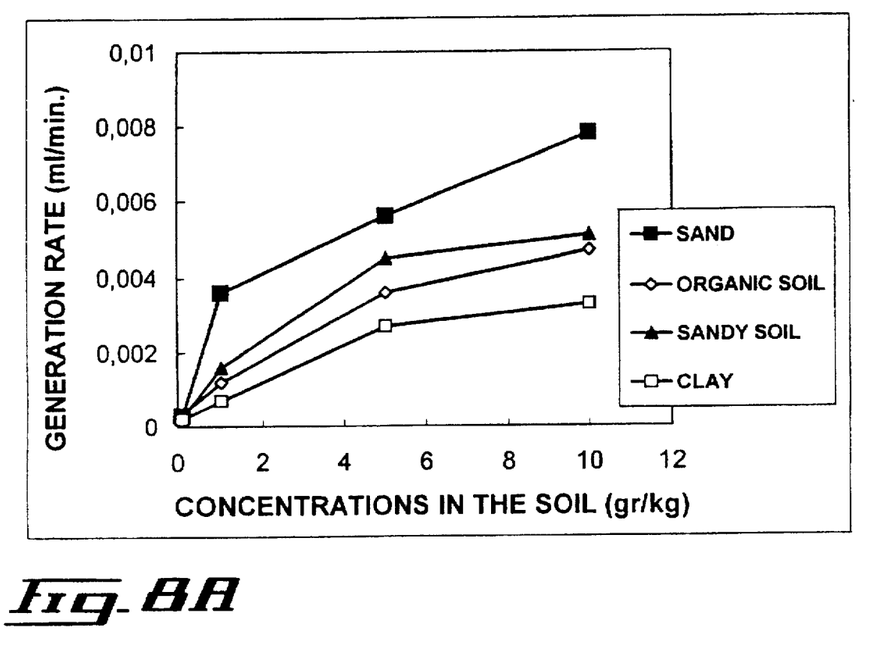
FIG. 8A is a graph plotting actual soil contamination of fuel oil in different types of dry soil compared to the generation rate of the volatile constituent.
Figure 8B:
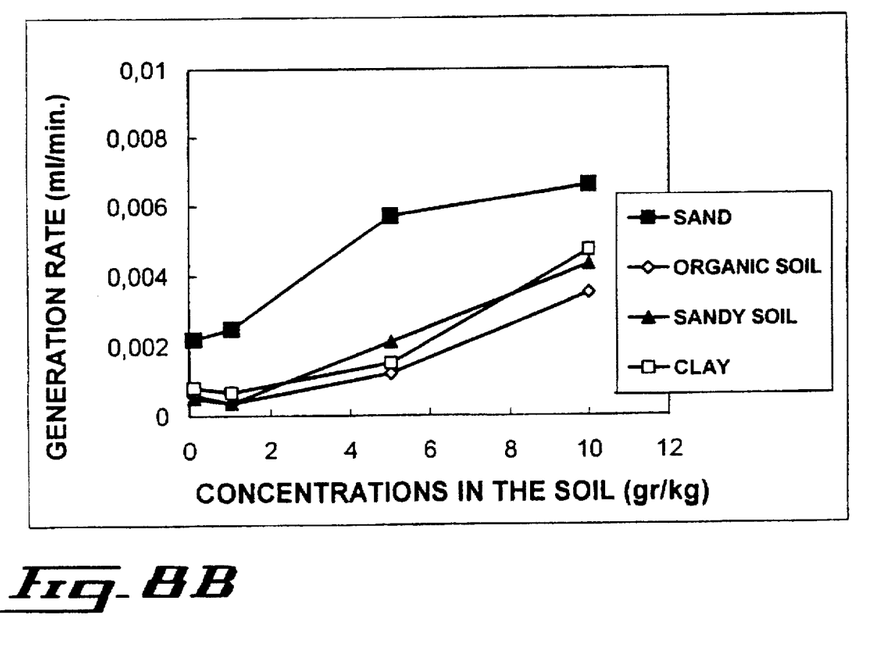
FIG. 8B is a graph similar to that of FIG. 8A except that the soil was wet.

FIGS. 8A and 8B are graphs illustrating the correlation between the actual soil contamination and the generation rate in the soil. FIG. 8A illustrates tests carried out on four different soil types—in sand, an organic soil, a sandy soil and a clay type soil. As will be seen, the types of soils will provide different readings but in general, there is a correlation between the vapor generation rate and the actual contamination.

FIG. 8B provides a similar comparison, but in a wet soil. Both FIGS. 8A and 8B utilize fuel oil as the contaminant.

Figure 9A:
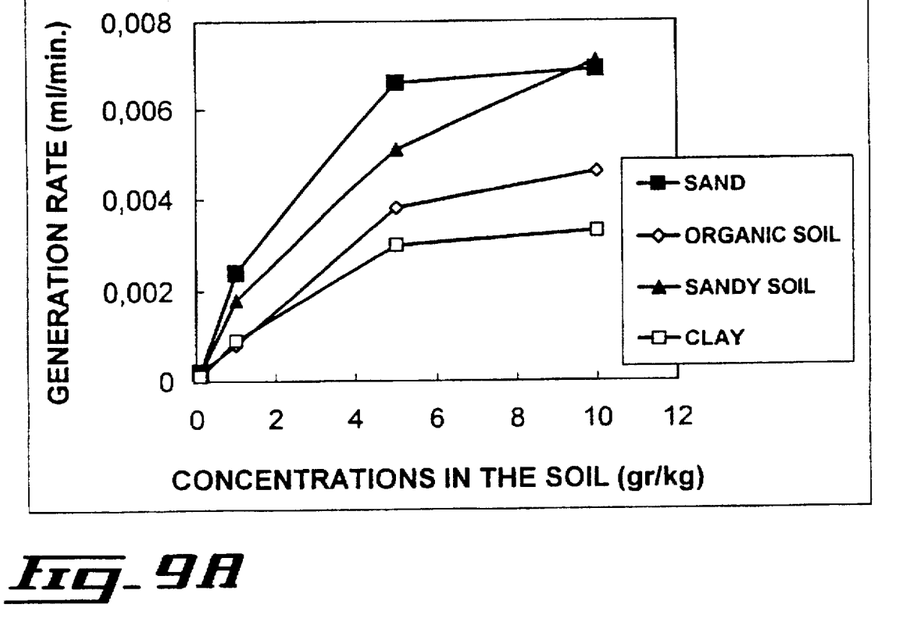
FIG. 9A is a graph plotting the soil contamination of diesel fuel in a dry soil compared to the generation rate of the volatile constituent.
Figure 9B:
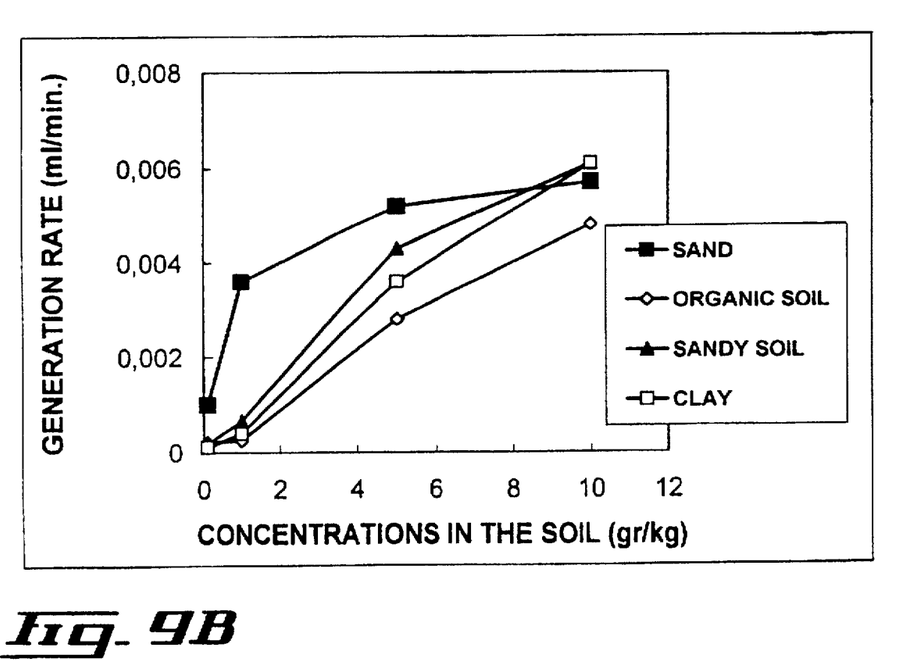
FIGS. 9B is a graph similar to FIG. 9A except in a wet soil.

FIGS. 9A and 9B are similar to FIGS. 8A and 8B except that diesel fuel was employed. Again, there is a correlation between the actual contaminant and the generation rate of the volatile constituent.

I claim:

1. A method for determining the relative presence of a first fluid in a soil volume, the method including the step of treating a soil volume by injecting a second fluid into said soil volume for a period of time sufficient to reduce the presence of said first fluid, characterized by the step of subsequently measuring the rate of increase of the concentration of said first fluid in said soil volume.

2. The method of measuring the degree of contamination of a soil volume by a contaminant which has a volatile constituent, the method including the step of injecting a non-contaminated gas into said soil volume for a period of time sufficient for a measurement of said volatile constituent to be reduced, characterized by the step of subsequently measuring the rate of increase of the concentration of said volatile constituent in said soil volume.

3. The method of claim 2 including the step of continuing to inject said non-contaminated gas at a reduced flow rate while measuring the concentration of the volatile constituent.

4. The method of claim 2 where in said injections of non-contaminated gas is stopped while measuring the concentration of said volatile constituent.

5. The method of claim 2 wherein said first gas is filtered air.

6. The method of claim 1, wherein said first fluid is a hydrocarbon having a volatile constituent, the method including measuring the concentration of said volatile constituent in said soil volume, continuing to measure the concentration of said volatile constituent while injecting said second fluid into said soil volume until the concentration level of said volatile constituent remains relatively stable, stopping the injection of said second fluid and measuring the rate of increase of the concentration of said volatile constituent.

7. The method of claim 6, wherein said second fluid is purified air.

* * * * *

UNITED STATES PATENT AND TRADEMARK OFFICE
CERTIFICATE OF CORRECTION

PATENT NO. : 5,786,527

DATED : July 28, 1998

INVENTOR(S) : Tartre

It is certified that error appears in the above-identified patent and that said Letters Patent is hereby corrected as shown below:

On the title page, item [19] and item [76] Inventor: "Tarte" should read --Tartre--.

Signed and Sealed this

Twenty-fourth Day of November, 1998

Attest:

BRUCE LEHMAN

Attesting Officer     Commissioner of Patents and Trademarks